(12) United States Patent
Kim et al.

(10) Patent No.: US 8,900,160 B2
(45) Date of Patent: Dec. 2, 2014

(54) PROBE AND DEVICE FOR DETECTING ABNORMALITY OF INTERVERTEBRAL DISC

(75) Inventors: Hyoung-Ihl Kim, Gwangju (KR);
Jong-Hyun Lee, Gwangju (KR);
Minhyun Jung, Gwangju (KR); Giseok Kang, Gwangju (KR)

(73) Assignee: Gwangju Institute of Science and Technology, Buk-Gu, Gwangju (KR)

( * ) Notice: Subject to any disclaimer, the term of this patent is extended or adjusted under 35 U.S.C. 154(b) by 7 days.

(21) Appl. No.: 13/306,396

(22) Filed: Nov. 29, 2011

(65) Prior Publication Data

US 2012/0136251 A1    May 31, 2012

(30) Foreign Application Priority Data

Nov. 29, 2010 (KR) .................. 10-2010-0119907

(51) Int. Cl.
*A61B 5/00*  (2006.01)
*A61B 8/12*  (2006.01)
*A61B 5/053* (2006.01)

(52) U.S. Cl.
CPC .............. *A61B 8/12* (2013.01); *A61B 5/4528* (2013.01); *A61B 5/4566* (2013.01); *A61B 5/6852* (2013.01); *A61B 5/0538* (2013.01); *A61B 5/0051* (2013.01)

USPC .......................................... 600/561

(58) Field of Classification Search
USPC ........................ 600/562–572, 587
See application file for complete search history.

(56) References Cited

U.S. PATENT DOCUMENTS

| 7,927,288 B2 * | 4/2011 | Gianchandani et al. ...... 600/561 |
| 2010/0004558 A1 * | 1/2010 | Frankhouser et al. ........ 600/567 |
| 2010/0094231 A1 * | 4/2010 | Bleich et al. .................. 604/274 |

* cited by examiner

*Primary Examiner* — Elmer Chao
(74) *Attorney, Agent, or Firm* — Nath, Goldberg & Meyer; Jerald L. Meyer

(57) ABSTRACT

The present invention relates to a probe and a device for detecting abnormality of an intervertebral disc. More particularly, the present invention relates to a probe and a device for detecting abnormality of an intervertebral disc that gives vibration stimulation to the inner part of the intervertebral disc and obtains an ultrasonic image in order to sense the abnormality of the intervertebral disc causing discogenic pains and inspects whether the intervertebral disc is abnormal by measuring impedance in the intervertebral disc. The present invention provides a probe for detecting abnormality of an intervertebral disc including: a shaft connector; a vibration generator connected to the shaft connector; and an inspector connected to the vibration generator, wherein the vibration generator vibrates the inspector by using a piezoelectric element and a device for detecting abnormality of an intervertebral disc.

11 Claims, 7 Drawing Sheets

(a)      (b)      (c)

PROBE AND DEVICE FOR DETECTING ABNORMALITY OF INTERVERTEBRAL DISC

CROSS-REFERENCE TO RELATED APPLICATION

This application claims under 35 U.S.C. §119(a) the benefit of Korean Patent Application No. 10-2010-0119907 filed on Nov. 29, 2010, the entire content of which is incorporated herein by reference.

BACKGROUND (a) Technical Field

The present invention relates to a probe and a device for detecting abnormality of an intervertebral disc. More particularly, the present invention relates to a probe and a device for detecting abnormality of an intervertebral disc that gives vibration stimulation to the inner part of the intervertebral disc and obtains an ultrasonic image in order to sense the abnormality of the intervertebral disc causing discogenic pains and inspects whether the intervertebral disc is abnormal by measuring the impedance in the intervertebral disc.

(b) Background Art

Low back pain or neck pain has been known as the next most common symptom to a cold with a probability that a person will suffer from the low back pain or neck pain at least once during life time is approximately 30%. Major factors causing the low back pain or neck pain may include lumbar arthralgia, spinal-pelvic arthralgia, discogenic pain, and disc herniation. Among them, disc herniation, commonly known as 'disc' is a disorder in which an intervertebral disc protrudes causing low back pain or neck pain and a nervous symptom. However, damages of a disc are more common etiology of pains than disc herniation.

Referring to FIG. 1, FIG. 1(a) shows the normal intervertebral disc, FIG. 1(b) shows a degeneratively changed intervertebral disc, and FIG. 1(c) shows an intervertebral disc in which a laceration is generated in annulus fibrosus. In the normal intervertebral disc 1, a sinu-vertebral nerve 3 is distributed along the edge of the annulus fibrosus 5. However, as the intervertebral disc is degeneratively changed, a sinu-vertebral nerve 3 is extended and distributed to the inside of the annulus fibrosus 5 and when the laceration 7 of the annulus fibrosus is generated in the annulus fibrosus 5, the sinu-vertebral nerve 3 is extended up to nucleus pulposus to cause an acute pain.

In recent years, the most accurate method for inspecting the intervertebral disc is known as magnetic resonance imaging (MRI). However, when a waist MRI was performed on normal persons with no low back pain or neck pain previously known, it was found that approximately 70% of them had abnormalities in the intervertebral disc. This fact indicates that the abnormalities of the intervertebral disc do not always lead to low back pain or neck pain. Further, it is still unclear whether the abnormalities discovered in the intervertebral disc from MRI performed on the patients with definite low back pain or neck pain are the main causes of such pain.

As a method of detecting the abnormality of the intervertebral disc, the intervertebral disc discography is a traditional technique that was first practiced in 1948. Even though its inherent technical value has been diminished over time, it has been proven to be effective as a modality to perform disc stimulation recently. In recent years, the intervertebral disc discography involves injecting a contrast material into the intervertebral disc and utilizes a graphical image to diagnose whether the intervertebral disc is abnormal. It can also be used to verify whether the abnormality of the intervertebral disc is the main cause of the low back pain or neck pain by observing patients feeling certain pains when the contrast medium is injected.

The inspection process of the discography will be described below in brief.

First, the patient lays face down on a bed and a waist of the patient is disinfected and thereafter, a needle (e.g., a diameter in the range of 22 to 25 gauge and a length of 5 inch) for injection is pierced obliquely (approximately at 45 degrees) while viewing a radioscope and the end of the needle is positioned at the center of the intervertebral disc.

Next, a syringe is filled with a constant material (displayed white in the radioscope because the contrast material is opaque to radiation) and connected to the needle for injection which is already inserted.

The contrast material diffused in the intervertebral disc is observed by using the radioscope while the contrast material is slowly injected to verify whether the patient complaints of pain. When the internal pressure of the intervertebral disc increases while the contrast material is filled in the intervertebral disc, a pain sensory nerve distributed in the intervertebral disc is stimulated, causing pain. When the same degree of low back pain or neck pain as the general low back pain or neck pain is caused during inspection, an inspection result is judged as positive and the inspected intervertebral disc is identified as the cause of the low back pain or neck pain.

The inner part of the intervertebral disc which is referred to as nucleus pulposusis primarily made of proteoglycan and collagen and contains moisture. Nucleus pulposus may be in a semi-solid state. Since the contrast material which is in a liquid state is injected in vertebral pulp, it takes time to evenly diffuse the contrast material. Accordingly, when an injection speed of the contrast material increases, higher pressure than general pressure is formed and when the injection speed of the contrast material decreases, lower pressure than the general pressure is formed. In this case, when the same degree of low back pain or neck pain as the general low back pain or neck pain is caused during inspection, an inspection result is judged as positive and the inspected intervertebral disc is identified as the cause of the low back pain or neck pain.

Since discography is performed in a manner in which an operator questions a degree of pain to the patient, the inspection can be completely fulfilled only when the pain sensory nerve distributed in the intervertebral disc is stimulated by the increased pressure. When the structure of annulus fibrosus in the intervertebral disc is maintained to some degree, the amount of the contrast material injected into nucleus pulposusis maintained as much, and as a result, the pressure is also increased. Therefore, pain may be caused to diagnose nucleus pulposusis by using the existing discography. However, when the contrast material injected into the intervertebral disc is leaked to the outside due to a severe degenerative change in the intervertebral disc, the increase in the internal pressure of the intervertebral disc cannot be expected, and as a result, stimulation of a nerve extended into the intervertebral disc is also not available, thereby not causing pain. In some cases, the nerve intends to be stimulated by rapidly injecting the contrast material, but a failure probability is high.

SUMMARY OF THE DISCLOSURE

The present invention has been made in an effort to provide a probe and a device for detecting abnormality of an intervertebral disc that can give a direct stimulation without injecting a contrast medium into the intervertebral disc.

Further, the present invention has been made in an effort to provide a probe and a device for detecting abnormality of an intervertebral disc that can verify the inner part of the intervertebral disc by irradiating ultrasonic waves to the inner part of the intervertebral disc and receiving an ultrasonic signal reflected in the inner part of the intervertebral disc.

Further, the present invention has been made in an effort to provide a probe and a device that are able to measure the impedance variations inside the intervertebral disc and detect intervertebral disc abnormality characterized by impedance variations.

According to an exemplary embodiment of the present invention, the invention includes: a shaft connector; a vibration generator connected to the shaft connector; and a detector connected to the vibration generator, wherein the vibration generator vibrates the inspector by using a piezoelectric element.

The vibration generator may include a first panel connected to the shaft connector and a second panel connected to the inspector and the first panel and the second panel may be connected to a vibration generating body formed by the piezoelectric element and a structure which is in a surface-contact with the vibration generating body.

The detector may include an ultrasonic transceiver generating ultrasonic waves and receiving the ultrasonic waves reflected in the intervertebral disc. Further, a conductive backing is provided at the rear end of the ultrasonic transceiver.

In the detector, the conductive backing may be provided in a cylindrical metallic pipe, the ultrasonic transceiver may be provided at the front end of the conductive backing, and a ground electrode may be provided at the front end of the ultrasonic transceiver.

The front surface of the detector may have any one of a circular, dome, or inclined cross sections.

Further, an insulating coating layer may be provided between the metallic pipe and the conductive backing, and the ground electrode may be electrically connected with the metallic pipe.

Meanwhile, the inspector of the probe for detecting abnormality of an intervertebral disc according to the exemplary embodiment of the present invention may further include a first electrode and a second electrode for measuring impedance in the intervertebral disc by applying predetermined voltage.

According to another exemplary embodiment of the present invention, there is provided a device for detecting abnormality of an intervertebral disc, which includes; a probe for detecting abnormality of an intervertebral disc; a shaft connected with the device for detecting abnormality of an intervertebral disc; and a vibration controlling unit for controlling a vibration generator of the device for detecting abnormality of an intervertebral disc.

The controlling unit may further include an ultrasonic controlling unit controlling an ultrasonic transceiver of the device for detecting abnormality of an intervertebral disc.

Further, the device for detecting abnormality of an intervertebral disc may further include an impedance probe having a first electrode and a second electrode for measuring impedance. The controlling unit may further include an impedance controlling unit for controlling the impedance probe.

According to exemplary embodiments of the present invention, since vibration stimulation can be directly given in an intervertebral disc without injecting a contrast medium into the intervertebral disc, an abnormal section of the intervertebral disc can be determined rapidly and easily.

Further, according to the exemplary embodiments of the present invention, an image of an infectious section can be acquired by generating and receiving ultrasonic waves. Moreover, according to the exemplary embodiments of the present invention, an abnormal section can be determined by measuring impedance in the intervertebral disc.

According to the exemplary embodiments of the present invention, a damage or abnormal section in the intervertebral disc can be accurately determined, and as a result, discogenic pain caused due to the abnormality of the intervertebral disc can be verified.

DETAILED DESCRIPTION

Figure 1:
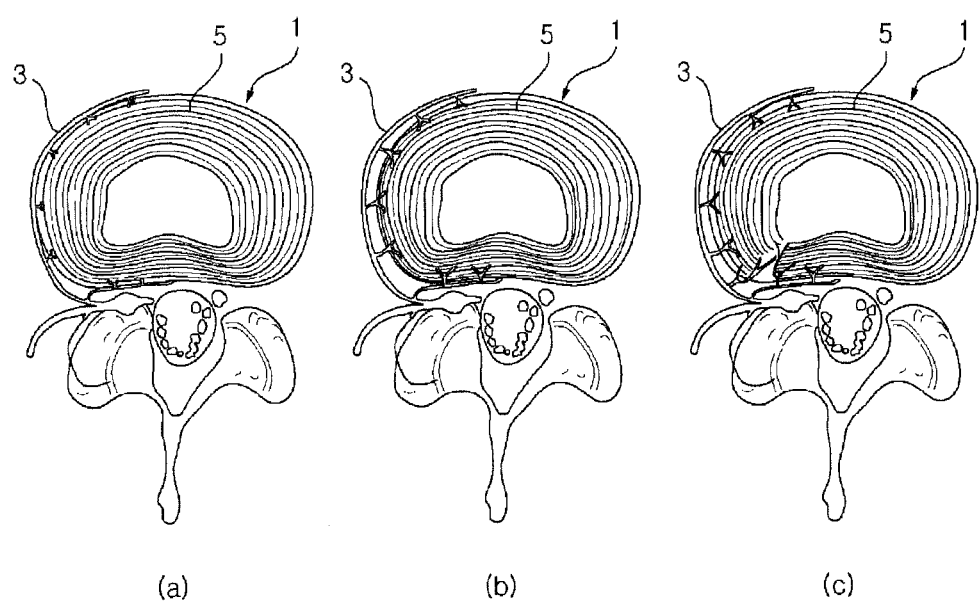
FIG. 1 is a diagram showing a normal intervertebral disc and an abnormal intervertebral disc.

Hereinafter, exemplary embodiments of the present invention will be described in detail with reference to the accompanying drawings. First of all, it is to be noted that in giving reference numerals to elements of each drawing, like reference numerals refer to like elements even though like elements are shown in different drawings. Further, in describing the present invention, well-known functions or constructions will not be described in detail since they may unnecessarily obscure the understanding of the present invention. Hereinafter, the exemplary embodiment of the present invention will be described, but it will be understood to those skilled in the art that the spirit and scope of the present invention are not limited thereto and various modifications and changes can be made by those skilled in the art.

Figure 2:
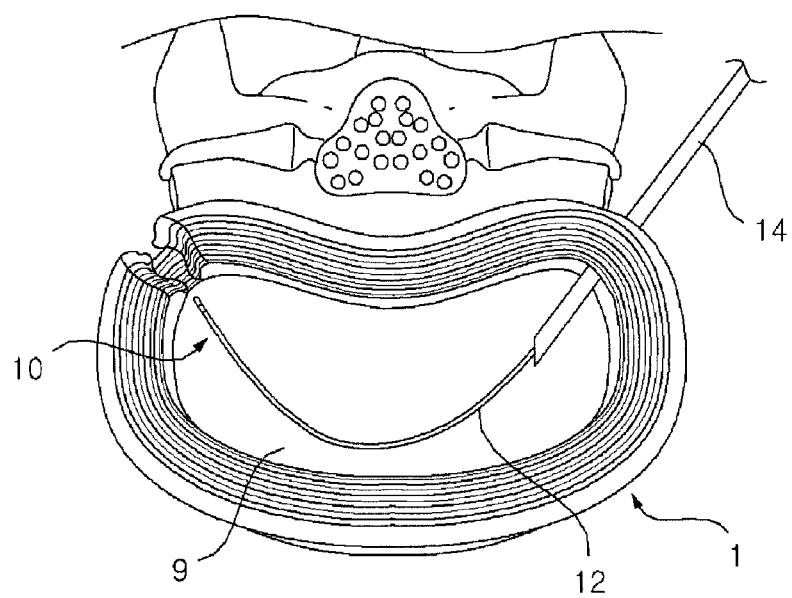
FIG. 2 is a diagram showing a state in which an intervertebral disc inspecting device is inserted into an intervertebral disc according to an exemplary embodiment of the present invention.

FIG. 2 is a diagram showing a state in which an intervertebral disc inspecting device is inserted into an intervertebral disc according to an exemplary embodiment of the present invention.

Referring to FIG. 2, the intervertebral disc inspecting device according to the exemplary embodiment of the present invention includes an inspection probe 10 for inspecting whether an intervertebral disc is abnormal, and a shaft 11 having the inspection probe 10 at the end thereof for connecting the inspection probe 10 to an external system not shown. An introducer needle 14 is inserted into the intervertebral disc 1 in order to insert the inspection probe 10 into the intervertebral disc 1. The introducer needle 14 has a hollow shape and the internal diameter thereof is preferably larger than the diameter of each of the inspection probe 10 and the shaft 11.

The inspection probe 10 inspects whether the intervertebral disc 1 is abnormal in vertebral pump 9 of the intervertebral disc 1 and determines whether annulus fibrosus is damaged or sinu-vertebral nerve is abnormally developed. When an inspection position is in advanced determined in the intervertebral disc 1, the inspection probe 10 may be moved to a predetermined inspection position/direction in the intervertebral disc by accurately adjusting an angle at which the introducer needle 14 is inserted into the intervertebral disc 1. However, since an abnormal position in the intervertebral disc 1 cannot be substantially estimated immediately, the inspection probe 10 is preferably set to be arbitrarily positioned in the intervertebral disc 1. To this end, a part or the entirety of the shaft 11 is formed to be flexible and is steered by the control from an external operator or inspection system.

As a configuration for steering the end of the shaft 11, the shaft 11 may be configured by a memory wire or a shape memory alloy. Alternatively, an electromechanical actuator or a steering catheter may be applied to the shaft 11.

Figure 3:
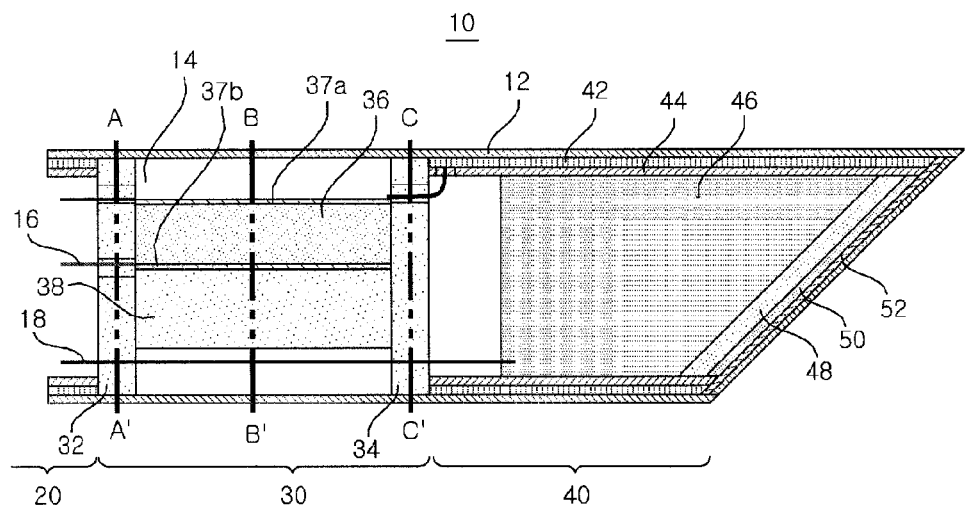
FIG. 3 is a cross-sectional view of an inspection probe of an intervertebral disc inspecting device according to an exemplary embodiment of the present invention and FIG. 4 is cross-sectional views taken along lines A-A', B-B', and C-C' of FIG. 3.
Figure 4:
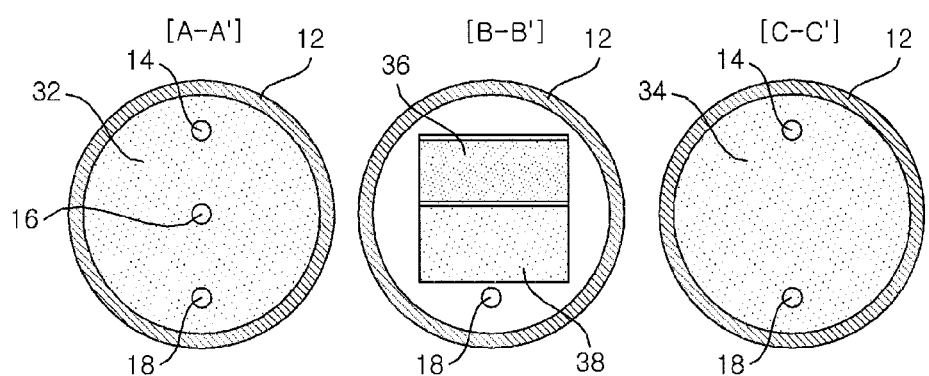

FIG. 3 is a cross-sectional view of an inspection probe of an intervertebral disc inspecting device according to an exemplary embodiment of the present invention and FIG. 4 is cross-sectional views taken along lines A-A', B-B', and C-C' of FIG. 3.

The inspection probe 10 includes a shaft connector 20, a vibration generator 30, and an inspector 40. An insulating tube 12 is provided or clad to the exterior of the inspection probe 10 to preferably electrically isolate the inside and the outside of the inspection probe 10 from each other.

The shaft connector 20 connects the inspection probe 10 to the shaft 11 (not shown in FIG. 3). Substantially, the shaft connector 20 may be appreciated as an extension structure of the shaft 11. The shaft connector 20 is preferably configured to be steeringable in order to adjust the position of the end of the inspection probe 10 as described above.

The vibration generator 30 as a configuration used to vibrate the inspector 40 may be formed to vibrate the inspector 40 up and down, left and right, or in a combination direction thereof. The vibration generator 30 includes a first panel 32 coupling the vibration generator 30 with the shaft connector 20, a second panel 34 coupling the vibration generator 30 with the inspector 40, and a vibration generating body 36 and a structure 38 which are formed by connecting the first panel 32 and the second panel 34 to each other and positioned between the first panel 32 and the second panel 34 similarly as a beam. Meanwhile, as shown in FIG. 3, the insulating tube 12 is clad on the outer peripheries of the shaft connector 30, the vibration generator 30, and the inspector 40. In FIG. 3, the insulating tube 12 is provided on even the exterior of the vibration generator 30. Herein, the insulating tube 12 serves to perform only an insulating function in the range of the vibration generator 30, but does not influence the structural connection between the first panel 32 and the second panel 34 of the vibration generator 30. The insulating tube 12 is preferably made of bio-compatible material such as parylene, PDMS, or SU-8.

The first panel 32 and the second panel 34 may have disc-shaped cross sections. In the exemplary embodiment, the vibration generating body 36 is configured by a piezoelectric element. The vibration generating body 36 preferably has a rectangular plane shape and one end of the vibration generating body 36 is coupled to the first panel 32 and the other end of the vibration generating body 36 is coupled to the second panel 34. The vibration generating body 36 is in surface-contact with the structure 38. The structure 38 receives contraction and expansion of the vibration generating body 36 to enable the second panel 34 coupled to the inspector 40 to vibrate horizontally or vertically. When the structure 38 has too large stiffness, a vibration width according to the contraction and expansion of the vibration generating body 36 may be very small, and as a result, the structure 38 is preferably flexible to some degree.

Referring to FIG. 3, a ground line and a vibration control line for controlling the contraction and expansion of the vibration generating body 36 are connected to the top surface and bottom surface of the vibration generating body 36. As the exemplary embodiment, the ground line 14 is connected to the top surface of the vibration generating body 36 and the vibration control line 16 is connected to the bottom surface of the vibration generating body 36. In the configuration, the contraction and expansion of the vibration generating body 36 is controlled by the polarity and magnitude of voltage supplied to the vibration control line 16 and a conversion frequency of the voltage polarity. The vibration generating body 36 is repeatedly contracted and expanded by the voltage (control signal) supplied through the vibration control line 16, but the structure 38 that is in surface-contact with the vibration generating body 36 is not contracted or expanded. Since the vibration generating body 36 and the structure 38 are in surface-contact with each other, the contraction and expansion of the vibration generating body 36 finally vibrates a joining structure of the vibration generating body 36 and the structure 38.

The inspector 40 is coupled to the second panel 34 to vibrate together according to the horizontal or vertical vibration of the second panel 34. The inspector 40 has a substantially cylindrical shape. The insulating tube 12 is clad on the exterior of the inspector 40, a metallic tube 42 is provided in the insulating tube 12, and an insulating coating layer 44 is provided in the metallic tube 42. A conductive backing 46 is provided in the insulating collating layer 44. An ultrasonic transceiver 48 is provided inside the front surface of the conductive packing 46, i.e., the front surface of the inspector 40. A ground electrode plate 52 is provided at the front end of the ultrasonic transceiver 48. A matching layer 50 is preferably provided between the ground electrode plate 52 and the ultrasonic transceiver 48.

The metallic tube 42 has a hollow cylindrical shape and forms the contour of the inspector 40. Moreover, the metallic tube 42 is made of a conductive material, such that when the ground line 14 connected to one electrode of the vibration generating body 36 is connected to the metallic tube 42, an additional ground line does not need to be provided up to the front surface of the inspector 40.

The conductive backing 46 is provided in the metallic tube 42 with the insulating coating layer 44 interposed therebetween. The ultrasonic transceiver 48 provided on the front surface of the conductive backing 46 serves to generate ultrasonic waves and receive the ultrasonic waves that is returned by being reflected by an external material. The ultrasonic transceiver 48 may be configured by a piezoelectric element that operates at a high frequency. An ultrasonic transmitting/receiving line 18 is connected to the conductive backing 46. The ultrasonic transmitting/receiving line 18 is connected to one end of the ultrasonic transceiver 48 through the conductive backing 46. In some cases, the ultrasonic transmitting/receiving line 18 may be connected directly to one end of the ultrasonic transceiver 48 without passing through the conductive backing 46. Meanwhile, the ground electrode plate 52 is provided at the front end of the ultrasonic transceiver 48 and as shown in FIG. 3, the ground electrode plate 52 is electrically connected with the metallic tube 42. Meanwhile, preferably, the matching layer 50 is provided between the ground electrode plate 52 and the ultrasonic transceiver 48 for impedance matching and the matching layer 50 may include conductive particles such as gold (Au), silver (Ag), or copper (Cu) to electrically connect the front surface of the ultrasonic transceiver 48 and the ground electrode plate 52.

The front shape of the inspector 10 may have a semicircular or circular shape, but may have a shape cut obliquely as shown in FIG. 3 in order to improve the directionality of ultrasonic transmission and reception.

Figure 5:
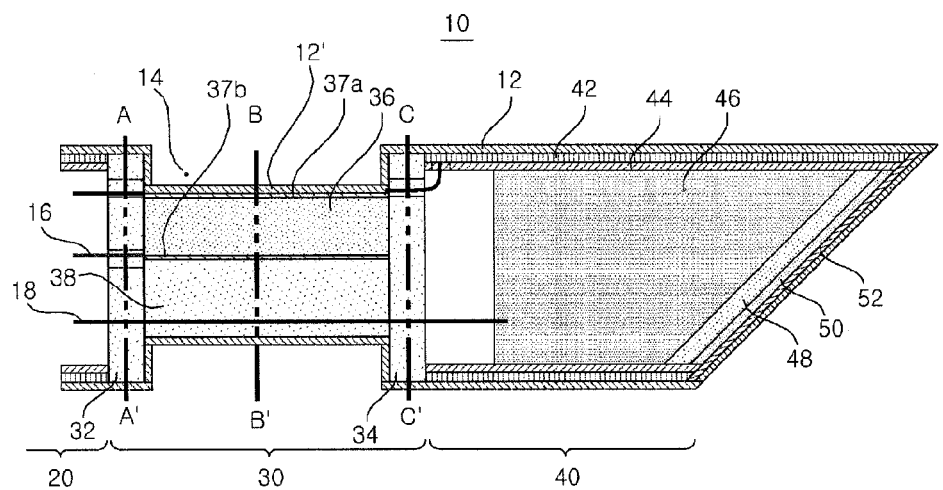
FIG. 5 is a cross-sectional view of an inspection probe of an intervertebral disc inspecting device according to another exemplary embodiment of the present invention and FIG. 6 is cross-sectional views taken along lines A-A', B-B', and C-C' of FIG. 5.
Figure 6:
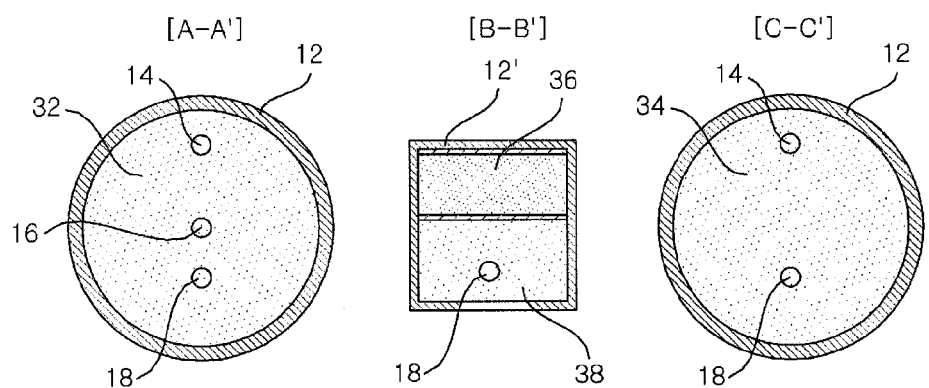

FIG. 5 is a cross-sectional view of an inspection probe of an intervertebral disc inspecting device according to another exemplary embodiment of the present invention and FIG. 6 is cross-sectional views taken along lines A-A', B-B', and C-C' of FIG. 5.

The configuration of the inspection probe 10 according to FIGS. 5 and 6 are substantially the same as the configuration of the inspection probe shown in FIGS. 3 and 4. The difference therebetween is that the insulating tube 12 is closed attached to the vibration generating body 36 and the structure 38 without an interval in an outer position of the vibration generator 30 in the configuration of the insulating tube 12 provided on the outer periphery of the inspection probe 10.

Referring back to FIG. 2, an operation of the intervertebral disc inspecting device according to the exemplary embodiment of the present invention described as above will be described below.

The inspection probe 10 connected to the shaft 11 is inserted through the introducer needle 14. The vibration generator 30 of the inspection probe 10 is vibrated with the inspection probe 10 moving to an internal position of the intervertebral disc 1 to be inspected. When stimulation is given to the inner part of the intervertebral disc 1 by the vibration, a patient s complains of pain in the case where a fissure is generated due to deformation or abnormality of the intervertebral disc 1 or sinu-vertebral nerve is extended abnormally. By the action, according to the exemplary embodiment of the present invention, whether patient's low back pain or neck pain is discogenic pain can be judged by giving the stimulation to the inner part of the intervertebral disc without injecting a contrasted medium.

Meanwhile, since the ultrasonic transceiver 48 is provided on the front surface of the inspection probe 10, the ultrasonic transceiver 48 generates the ultrasonic waves and receives an ultrasonic signal to acquire an ultrasonic image in the intervertebral disc 1.

Figure 7:
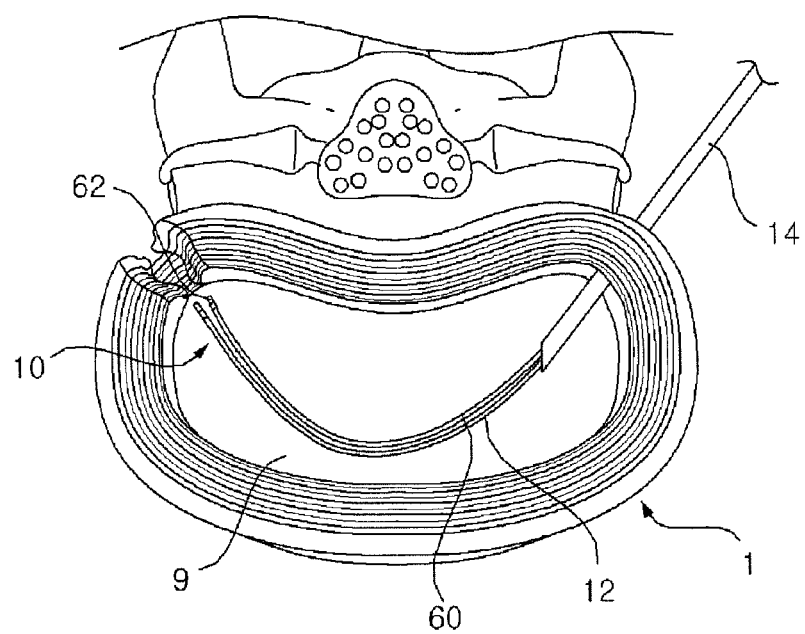
FIG. 7 is a diagram showing an example in which an impedance probe is used together with an inspection probe in a device for detecting abnormality of an intervertebral disc according to an exemplary embodiment of the present invention.

FIG. 7 is a diagram showing an example in which an impedance probe is used together with the inspection probe in the intervertebral disc inspecting device according to the exemplary embodiment of the present invention.

An impedance probe 62 is inserted into the nucleus pulposus (i.e., the intervertebral disc) through the introducer needle 14 together with the inspection probe 10. In this case, the impedance probe 62 is provided separately from the inspection probe 10. The impedance probe 62 is provided at the end of an impedance probe shaft 60 and a configuration of the impedance probe shaft 60 is substantially the same as the configuration of the shaft 11 of the inspection probe 10.

The impedance probe 62 has a first electrode and a second electrode at the end thereof. The first electrode and the second electrode are exposed in the nucleus pulposus 9 of the intervertebral disc 1. When a current value flowing between the first electrode and the second electrode is measured while predetermined voltage is applied to the first electrode and the second electrode, local impedance may be calculated at a point where the impedance probe 62 is positioned.

A point where the measured impedance decreases is judged the damaged section of the intervertebral disc 1. The reason therefor is that a section where the fissure is generated or a section where a nerve grows to the inner part of the intervertebral disc 1 has lower impedance than a normal internal point of the intervertebral disc 1.

The impedance probe 62 is adjusted to be positioned adjacent to the inspection probe 10. The impedance probe 62 measures impedance together at a point where the patient complaints of pain by a vibration stimulation of the inspection probe 10 to judge whether the corresponding point is abnormal together. Moreover, the ultrasonic transceiver 48 of the inspection probe 10 generates the ultrasonic waves and receives the reflected ultrasonic waves to provide an ultrasonic image of an abnormal infectious section.

Figure 8:
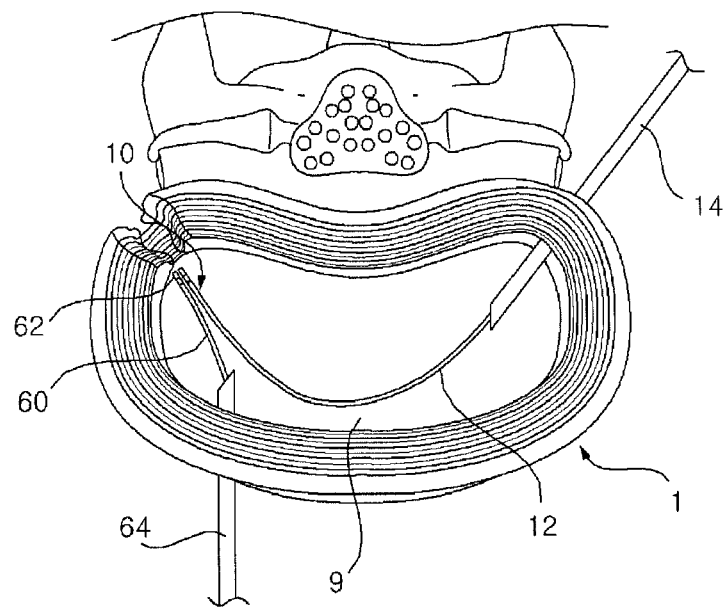
FIG. 8 is a diagram showing another example in which the impedance probe is used together with the inspection probe in the device for detecting abnormality of an intervertebral disc according to the exemplary embodiment of the present invention.

FIG. 8 is a diagram showing another example in which an impedance probe is used together with the inspection probe in the intervertebral disc inspecting device according to the exemplary embodiment of the present invention.

In FIG. 8, an example in which an additional introducer needle 64 for the impedance probe 62 is inserted into the intervertebral disc and the impedance probe 62 is positioned adjacent to the inspection probe 10 through the additional introducer needle 64 in the intervertebral disc is shown.

Meanwhile, referring to FIGS. 7 and 8, the impedance probe 62 is provided separately from the inspection probe 10. However, in the exemplary embodiment of the present invention, actually, the inspection probe 10 may, of course, further include the first electrode and the second electrode for measuring impedance. When the inspection probe 10 includes the first electrode and the second electrode at the end or outer periphery thereof, the vibration stimulation, the acquisition of the ultrasonic waves, and the measurement of the impedance can be all performed in the intervertebral disc 1 by using one device.

Figure 9:
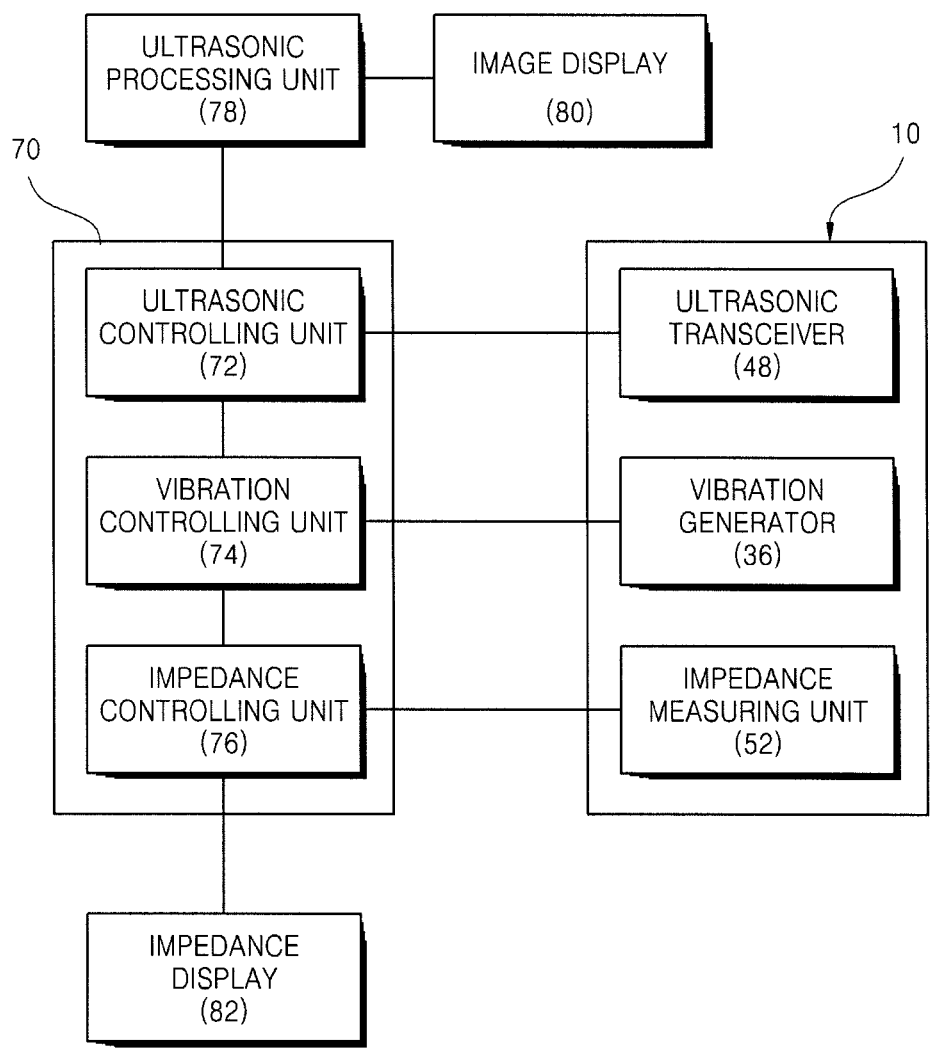
FIG. 9 is a block diagram showing a configuration of the entire device for detecting abnormality of the intervertebral disc according to the exemplary embodiment of the present invention.

FIG. 9 is a block diagram showing a configuration of the entire device for detecting abnormality of an intervertebral disc according to the exemplary embodiment of the present invention.

According to FIG. 9, the device for detecting abnormality of an intervertebral disc according to the exemplary embodiment of the present invention includes the inspection probe 10 and the impedance probe 62 and a controller 70 for controlling the inspection probe 10 and the impedance probe 62. The controller 70 includes an ultrasonic controlling unit 72, a vibration controlling unit 74, and an impedance controlling unit 76.

The ultrasonic controlling unit 72 transmits an ultrasonic wave generation signal to the ultrasonic transceiver 48 of the inspection probe 10 through the ultrasonic transmitting/receiving line 18 and receives a reflected ultrasonic signal through the ultrasonic transmitting/receiving unit 48. The ultrasonic controlling unit 72 transmits the received reflected ultrasonic signal to an ultrasonic processing unit. The ultrasonic processing unit 78 processes the generated ultrasonic signal and the received reflected ultrasonic signal to process the signals into an image of a predetermined section and thereafter, output image data through an image display 80.

The vibration controlling unit 74 transmits a vibration control signal to the vibration generating body 36 through the vibration control line 16. The vibration control is preferably achieved with magnitude and frequency information of vibration.

The impedance controlling unit 76 serves to apply predetermined voltage to the first electrode and the second electrode of the impedance probe 62 and calculate resulting impedance. Preferably, the calculated impedance information is visually outputted through an impedance display 82.

Meanwhile, the impedance probe 62 may be provided separately from the inspection probe 10, but a function of the impedance probe 62 may, of course, be integrated into the inspection probe 10.

Further, by using additional laser treatment equipment together with the inspection probe 10, an accurate position of the section in the intervertebral disc which is abnormal is determined and thereafter, a laser treatment is preferably performed immediately.

The spirit of the present invention has just been exemplified. It will be appreciated by those skilled in the art that various modifications, changes, and substitutions can be made without departing from the essential characteristics of the present invention. Accordingly, the exemplary embodiments disclosed in the present invention and the accompanying drawings are used not to limit but to describe the spirit of the present invention. The scope of the present invention is not limited only to the embodiments and the accompanying drawings. The protection scope of the present invention must be analyzed by the appended claims and it should be analyzed that all spirits within a scope equivalent thereto are included in the appended claims of the present invention.

What is claimed is:

1. A probe for detecting abnormality of an intervertebral disc, comprising:
    a shaft connector;
    a vibration generator connected to the shaft connector, the vibration generator further comprising:
    a first panel which couples the vibration generator to the shaft connector,
    a second panel which couples the vibration generator to an inspector,
    wherein the second panel vibrates horizontally and vertically, and
    a vibration generating body and a structure, located between and connecting the first and second panels,
    wherein the structure is flexible and in surface-contact with the vibration generating body; and
    the inspector connected to the vibration generator,
    wherein the inspector has a substantially cylindrical shape, a front surface with a conductive backing, and vibrates with said second panel horizontal and vertical vibration; and
    wherein the vibration generator is located between the shaft connector and the inspector and wherein the vibration generator body is formed by a piezoelectric element, and the vibration generator is configured to vibrate the inspector.

2. The probe for detecting abnormality of an intervertebral disc of claim 1, wherein the inspector includes an ultrasonic transceiver generating ultrasonic waves and receiving the ultrasonic waves reflected in the intervertebral disc.

3. The probe for detecting abnormality of an intervertebral disc of claim 2, wherein in the inspector, the conductive backing is provided in a cylindrical metallic pipe, the ultrasonic transceiver is provided at a front end of the conductive backing, and a ground electrode is provided at a front end of the ultrasonic transceiver.

4. The probe for detecting abnormality of an intervertebral disc of claim 3, wherein the front surface of the inspector has any one of a circular, dome, and inclined cross sections.

5. The probe for detecting abnormality of an intervertebral disc of claim 3, wherein an insulating coating layer is provided between the metallic pipe and the conductive backing, and
    the ground electrode is electrically connected with the metallic pipe.

6. The probe for detecting abnormality of an intervertebral disc of claim 1, wherein the inspector further includes a first electrode and a second electrode for measuring impedance in the intervertebral disc by applying predetermined voltage.

7. A device for detecting abnormality of an intervertebral disc, comprising:
    a probe for detecting abnormality of an intervertebral disc of claim 1;
    a shaft connected with the device for detecting abnormality of an intervertebral disc; and
    a vibration controlling unit for controlling a vibration generator of the device for detecting abnormality of an intervertebral disc.

8. The device for detecting abnormality of an intervertebral disc of claim 7, wherein the controlling unit further includes an ultrasonic controlling unit controlling an ultrasonic transceiver of the device for detecting abnormality of an intervertebral disc.

9. The device for detecting abnormality of an intervertebral disc of claim 7, further comprising:
    an impedance probe having a first electrode and a second electrode for measuring impedance.

10. The device for detecting abnormality of an intervertebral disc of claim 9, wherein the controlling unit further includes an impedance controlling unit for controlling the impedance probe.

11. The device of claim 1, wherein the vibration generator is configured to vibrate the inspector up and down along an axis of the inspector, left and right perpendicular to the axis of the inspector, or in a combination direction thereof.

* * * * *